US00PP27228P3

(12) United States Plant Patent
Klemm et al.

(10) Patent No.: US PP27,228 P3
(45) Date of Patent: Oct. 4, 2016

(54) POINSETTIA PLANT NAMED 'NPCW14233'

(50) Latin Name: *Euphorbia pulcherrima*
Varietal Denomination: NPCW14233

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 120 days.

(21) Appl. No.: 14/544,329

(22) Filed: Dec. 23, 2014

(65) Prior Publication Data

US 2016/0183435 P1 Jun. 23, 2016

(51) Int. Cl.
*A01H 5/02* (2006.01)

(52) U.S. Cl.
USPC ..... Plt./303

(58) Field of Classification Search
USPC ..... Plt./303
See application file for complete search history.

(56) References Cited

PUBLICATIONS

UPOV hit on CA PBR 14-8506, Dec. 19, 2014.*
UPOV hit on QZ PBR 20143341 Dec. 11, 2014.*

* cited by examiner

*Primary Examiner* — Anne Grunberg
(74) *Attorney, Agent, or Firm* — James M. Weatherly; Bethany R. Roahrig; Cochran Freund & Young, LLC

(57) ABSTRACT

A new poinsettia plant particularly distinguished by having greenish to apricot colored bracts with dense reddish spots and stripes, medium vigor, and an upright habit, is disclosed.

1 Drawing Sheet

Genus and species: *Euphorbia pulcherrima.*
Variety denomination: 'NPCW 14233'.

BACKGROUND OF THE NEW PLANT

The present invention comprises a new and distinct variety of poinsettia, botanically known as *Euphorbia pulcherrima* and hereinafter referred to by the variety name 'NPCW14233'. 'NPCW14233' is a selection from a branch mutation from the poinsettia variety 'NPCW10158' (U.S. Plant Pat. No. 22,580).

In November/December of 2008 a branch mutation was discovered on the poinsettia variety 'NPCW10158' in Nairobi, Kenya. Vegetative cuttings of the branch mutation were taken and propagated. In October of 2009, a single plant was selected in Stuttgart, Germany. In May of 2010, 'NPCW14233' was first asexually propagated by apical vegetative cuttings. 'NPCW14233' was found to reproduce true to type in successive generations of asexual propagation via apical vegetative cuttings in Stuttgart, Germany.

SUMMARY

The following are the most outstanding and distinguishing characteristics of this new variety when grown under normal horticultural practices in Stuttgart, Germany.

1. Greenish to apricot colored bracts with dense reddish spots and stripes;
2. Medium vigor; and
3. An upright habit.

DESCRIPTION OF THE PHOTOGRAPH

This new poinsettia plant is illustrated by the accompanying photograph, which shows an overall view of the plant.

The photograph is of a plant approximately four-months-old grown indoors in Stuttgart, Germany in October 2013. The colors shown are as true as can be reasonably obtained by conventional photographic procedures.

DESCRIPTION OF THE NEW VARIETY

The following detailed descriptions set forth the distinctive characteristics of 'NPCW14233'. The data which define these characteristics were collected from asexual reproductions carried out in Stuttgart, Germany. Data was collected on plants 19 weeks after potting in a greenhouse in Stuttgart, Germany in the fall of 2014. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW 14233'.

Parentage: Branch mutation from the poinsettia variety 'NPCW10158'(U.S. Plant Pat. No. 22,580).

Growth:
- *Time to produce a rooted cutting.*—4 weeks.
- *Blooming habit.*—Intermittent.
- *Flowering response time.*—Approximately 57 days.
- *Keeping quality.*—Good.

Plant description:
- *Form.*—Triangular.
- *Growth habit.*—Upright.
- *Height.*—25.0 cm to 28.0 cm.
- *Width.*—23.0 cm to 28.0 cm.
- *Number of branches.*—6.5.
- *Average number of inflorescences per plant.*—6.5.

Propagation:
*Type cuttings.*—Apical cuttings.
*Time to produce a rooted cutting.*—4 weeks.
Stems:
*Color.*—RHS 143C.
*Length.*—23.0 cm to 25.0 cm.
*Internode length.*—1.0 cm to 2.5 cm.
*Diameter.*—0.5 cm to 0.8 cm.
Leaves:
*Quantity.*—5 to 7 per lateral branch.
*Arrangement.*—Alternate.
*Shape.*—Ovate.
*Apex.*—Acute.
*Base.*—Obtuse.
*Margin.*—Serrate.
*Lobes.*—Lobation characteristics: Shallow to moderate. Texture (both surfaces): Smooth. Vein color: Upper surface: Transparent. Lower surface: RHS 139D.
*Variegation.*—Absent.
*Size.*—Length: 8.0 cm to 13.0 cm. Width: 5.0 cm to 8.0 cm.
*Color.*—Mature foliage: Upper surface: RHS 139A. Lower surface: RHS N138B. Immature foliage: Upper surface: RHS 141A. Lower surface: RHS 139B.
*Leaf petiole.*—Length: 3.0 cm to 5.0 cm. Diameter: 0.2 cm to 0.3 cm. Color: Upper surface: RHS 139D with dense spots and stripes (reddish). Lower surface: RHS 139D with only shallow spots and stripes (reddish).
Inflorescence:
*Lastingness of inflorescence on the plant.*—3 to 4 weeks.
*Diameter.*—20.0 cm to 23.0 cm.
*Height.*—2.0 cm to 3.0 cm.
*Fragrance.*—Absent.
Bracts:
*Number of bracts per inflorescence.*—10 to 11.
*Shape.*—Ovate.
*Apex.*—Acute.
*Base.*—Obtuse.
*Margin.*—Mostly entire.
*Size.*—Length: 5.0 cm to 10.0 cm. Width: 3.0 cm to 8.0 cm.
*Texture.*—Upper and lower surfaces: Smooth.
*Vein color.*—Upper surface: RHS 144B. Lower surface: RHS 144D.
*Bract color.*—Upper surface: Greenish to apricot (basic color) RHS 11D with very dense spots in reddish between RHS 53B and RHS 46A (less intensive on older bracts/more intensive on small, young bracts in the center of the inflorescence). Lower surface: The same as upper surface.
*Bract petiole.*—Length: 0.5 cm to 2.0 cm. Diameter: 0.2 cm to 0.3 cm. Color: Upper surface: RHS 144D. Lower surface: RHS 144D with shallow spots and stripes (reddish).
Cyme:
*Diameter.*—1.0 cm to 1.5 cm.
*Cyathia number.*—4 to 6 per inflorescence.
*Cyathium.*—Shape: Ovate. Diameter: 0.2 cm to 0.4 cm. Length: 0.3 cm to 0.6 cm. Color: RHS 142B.
*Peduncle.*—Color: RHS 142B. Length: 0.2 cm.
*Nectar cups.*—Number: 1 per cyathium. Diameter: 0.1 cm. Size: 0.3 cm to 0.4 cm. Color: RHS 1C.
Reproductive organs:
*Stamens.*—Quantity: 5 to 10 per cyathium. Shape: Ovate.
*Filament.*—Length: 0.25 cm. Color: RHS 47C.
*Pollen.*—Quantity: Sparse. Color: RHS 11B.
Disease and insect/pest resistance: Nothing observed.
Fruit and seed set: No fruit or seed set have been observed.

COMPARISON WITH PARENTAL LINE AND KNOWN VARIETY

'NPCW 14233' is distinguished from its parents as described in Table 1:

TABLE 1

Comparison with Parental Line

| Trait | Variety 'NPCW14233' | Mutation parent 'NPCW10158' |
|---|---|---|
| Bract Color | Greenish to apricot colored bracts with dense reddish spots and stripes | Medium red bracts |

'NPCW 14233' is most similar to the commercial poinsettia plant named 'Monet Early Red' (unpatented in the U.S.). Differences between the two varieties are described in Table 2:

TABLE 2

Comparison with Similar Variety

| Trait | Variety 'NPCW14233' | Commercial line 'Monet Early Red' |
|---|---|---|
| Vigor | Medium vigor | Lower vigor |
| Earliness | Later than 'Monet Early Red' | Earlier than 'NPCW14233' |

We claim:

1. A new and distinct variety of poinsettia plant named 'NPCW 14233' as illustrated and described herein.

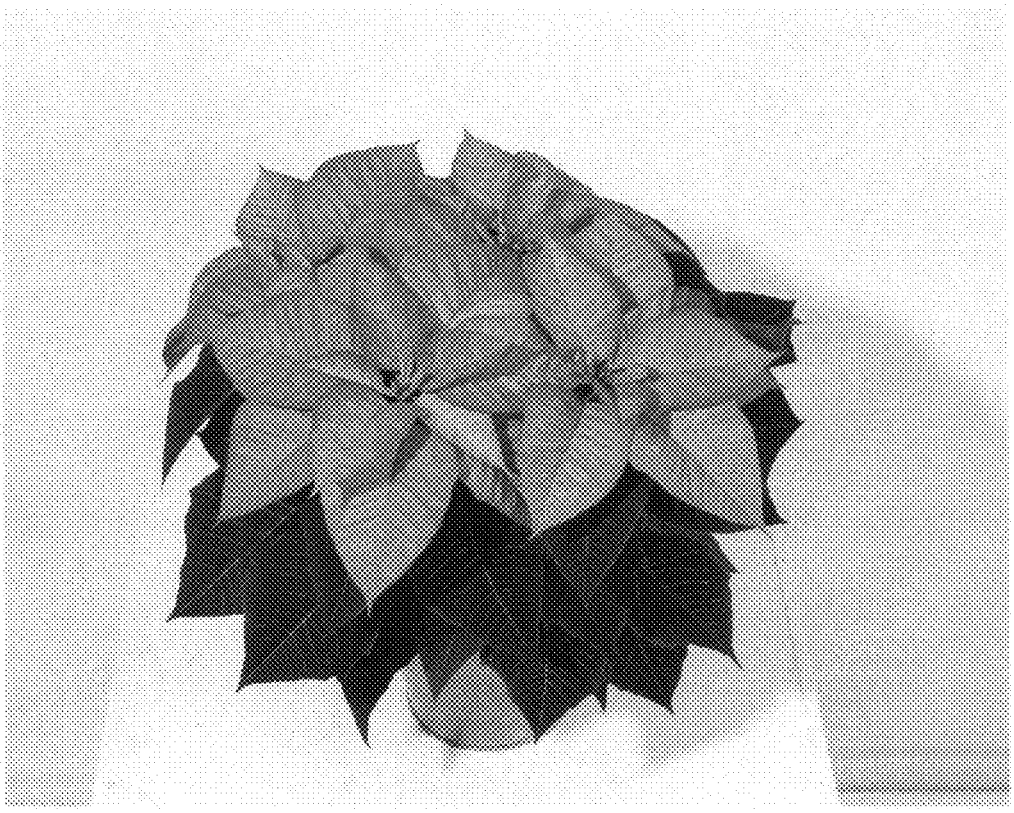

* * * * *